United States Patent
Martin et al.

[11] Patent Number: 5,213,103
[45] Date of Patent: May 25, 1993

[54] APPARATUS FOR AND METHOD OF COOLING ULTRASONIC MEDICAL TRANSDUCERS BY CONDUCTIVE HEAT TRANSFER

[75] Inventors: Glenn Martin; Hamid Ekhlassi, both of Chandler, Ariz.

[73] Assignee: Acoustic Imaging Technologies Corp., Phoenix, Ariz.

[21] Appl. No.: 830,224

[22] Filed: Jan. 31, 1992

[51] Int. Cl.$^5$ .............................................. A61B 8/00
[52] U.S. Cl. ............................ 128/660.07; 128/661.01
[58] Field of Search ....................... 128/660.01, 660.07, 128/661.01, 662.03–662.06; 73/618, 620, 625–626, 633

[56] References Cited

U.S. PATENT DOCUMENTS

| | | |
|---|---|---|
| 4,501,151 | 2/1985 | Christman .................. 128/660.01 X |
| 4,748,985 | 6/1988 | Nagasaki et al. ........... 128/662.03 X |
| 4,949,708 | 8/1990 | Tahayama et al. ......... 128/662.03 X |
| 5,076,276 | 12/1991 | Sakurai et al. ................. 128/660.01 |

Primary Examiner—Francis Jaworski
Attorney, Agent, or Firm—Christie, Parker & Hale

[57] ABSTRACT

A method for transferring heat away from an ultrasonic medical transducer having a face wherein heat is generated. The method is accomplished by positioning a heat sink behind the transducer face, securing the heat sink to a braided power cable, applying a heat conductive epoxy to the heat sink, and assembling a plastic housing around the heat sink. The transducer face is cooled by conductive heat transfer by transferring the heat into the heat sink, then transferring the heat into the epoxy, then transferring the heat into the power cable and the plastic housing before finally dissipating into the surrounding air.

25 Claims, 4 Drawing Sheets

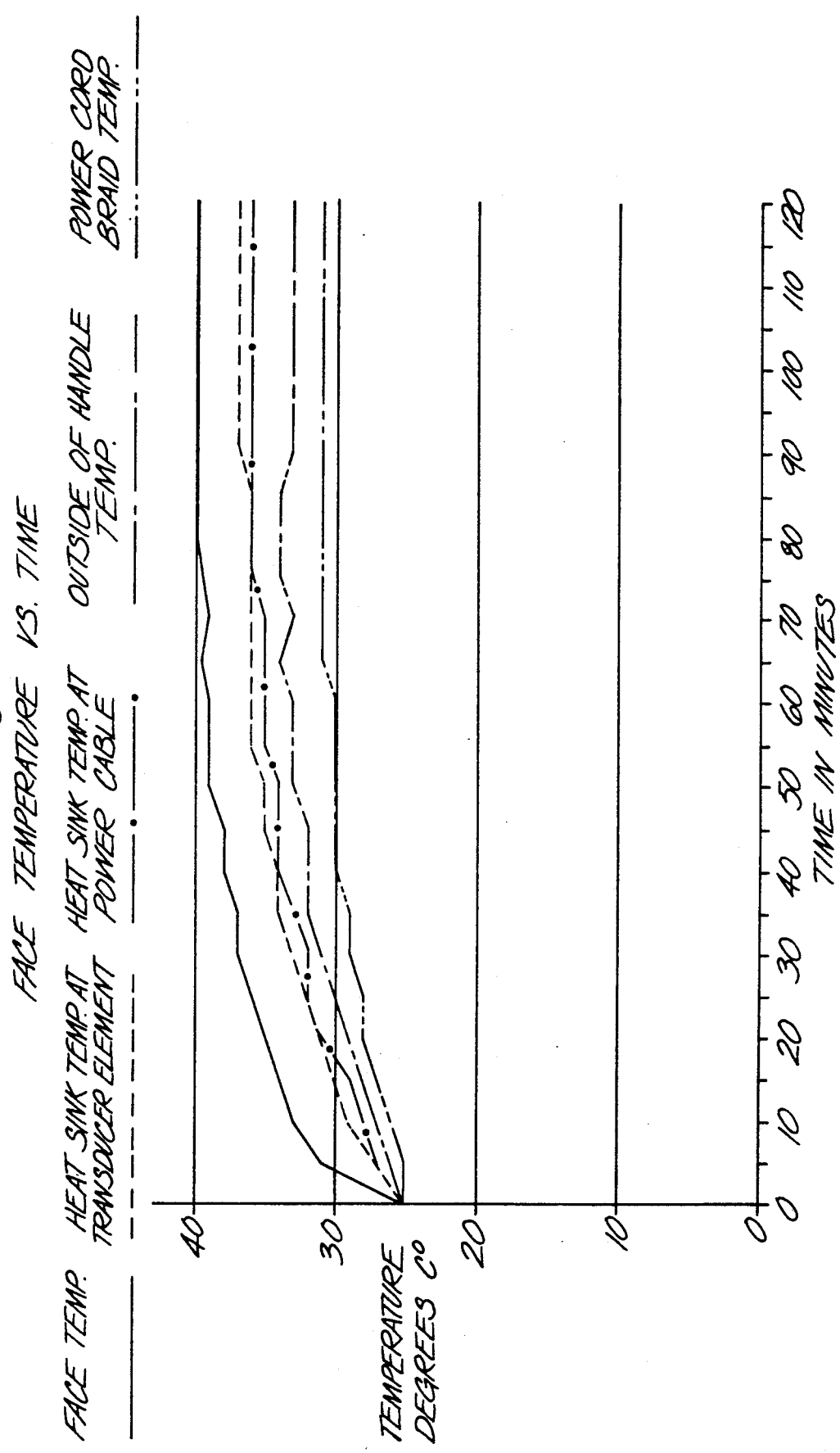

APPARATUS FOR AND METHOD OF COOLING ULTRASONIC MEDICAL TRANSDUCERS BY CONDUCTIVE HEAT TRANSFER

FIELD OF THE INVENTION

This invention generally relates to the field of ultrasonic medical transducer assemblies, and, more particularly, to an apparatus and method for cooling the transducer by conductive heat transfer.

BACKGROUND OF THE INVENTION

Ultrasonic medical transducers are used to observe the internal organs of a patient. Such an apparatus produces the display of successive images at a rapid rate so that an observer can see movements of an organ in "real time." Ultrasonic transducer assemblies are manufactured in a number of configurations including curved arrays, linear arrays, and non-array transducers such as doppler and concentric transducers, to name a few. The type of configuration of transducer used for a given application depends upon the type of medical observation to be performed. By way of example, a curved array transducer produces an image over a wider field of view and thus permits the observer to view objects that would ordinarily be hidden from view when using a linear array. For example a bone, such as a rib may obstruct the view of an internal organ.

A problem associated with all ultrasonic transducers is that during the scanning mode the face temperature of the transducer increases. The heating of the transducer face is directly related to the power supplied to the transducer elements located in the transducer face. It is desirable to supply sufficient power to the transducer elements because more power results in deeper penetration by the ultrasonic signals, yielding significantly clearer images.

The Federal Food and Drug Administration (FDA) has prescribed regulatory standards which limit the face temperature and the ultrasound intensity, i.e., power output of the transducer for product safety reasons, as well as to prevent unhealthy bioeffects. The present standard is that the face temperature of the transducer may not exceed 41° C. The practical effect of the FDA standards is that the desired ultrasonic penetration cannot be reached because operation at the power limit would result in exceeding the allowable transducer face temperature. Under certain scanning mode conditions, the desired intensity limits cannot be reached because face heating is the first limiting parameter reached. Therefore, a method for cooling the ultrasonic transducer face is necessary so that the transducer can operate at optimum power levels for deeper penetration and clearer images.

SUMMARY OF THE INVENTION

A presently preferred embodiment of the invention provides a method for cooling ultrasonic medical transducers by conductive heat transfer, whereby a heat sink device is placed behind the transducer elements which conducts heat away from the transducer face via thermal conduction and dissipates the heat through the handle of the transducer and/or a grounded power cable attached to the transducer.

The heat sink located behind the transducer elements preferably extends the entire length of the transducer handle. The heat sink is comprised of three separate pieces which encapsulate the electronics located within the transducer and clamp the power cable entering the rear of the transducer, which is also electrically connected to the electronics. After the heat sink has been placed behind the transducer elements a heat conductive epoxy is applied to the heat sink and a plastic housing is assembled around the heat sink. The heat conductive epoxy fills any gaps between the housing and the heat sink.

BRIEF DESCRIPTION OF THE DRAWINGS

These and other features and advantages of the present invention will be better understood by reference to the following detailed description when considered in conjunction with the accompanying drawings wherein:

FIG. 5 is a graph depicting the temperature of the transducer incorporating a heat sink according to the invention as a function of time.

DETAILED DESCRIPTION

Figure 1:
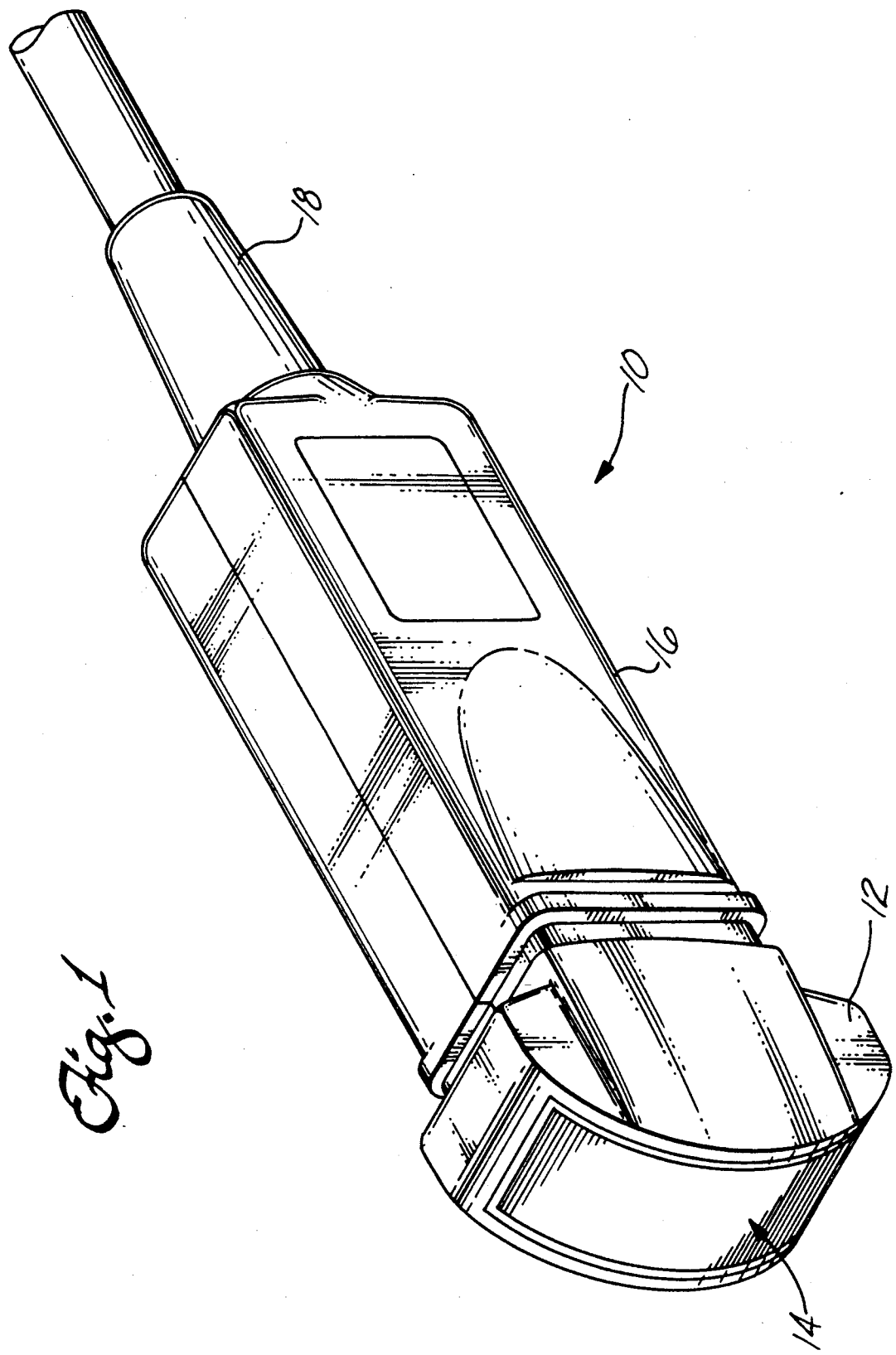
FIG. 1 is a perspective view of an ultrasonic medical transducer.

An exemplary ultrasonic medical transducer 10 can be seen in FIG. 1. The transducer consists of a head 12 upon which is located the face 14, a handle 16 and a power cable 18 entering the rear of the handle opposite the head of the transducer. In this particular embodiment the transducer elements located in the face of the transducer take the form of a curved array. The invention can be applied to other forms of transducers such as a linear array or a non-array transducer such as doppler and concentric.

Figure 2:
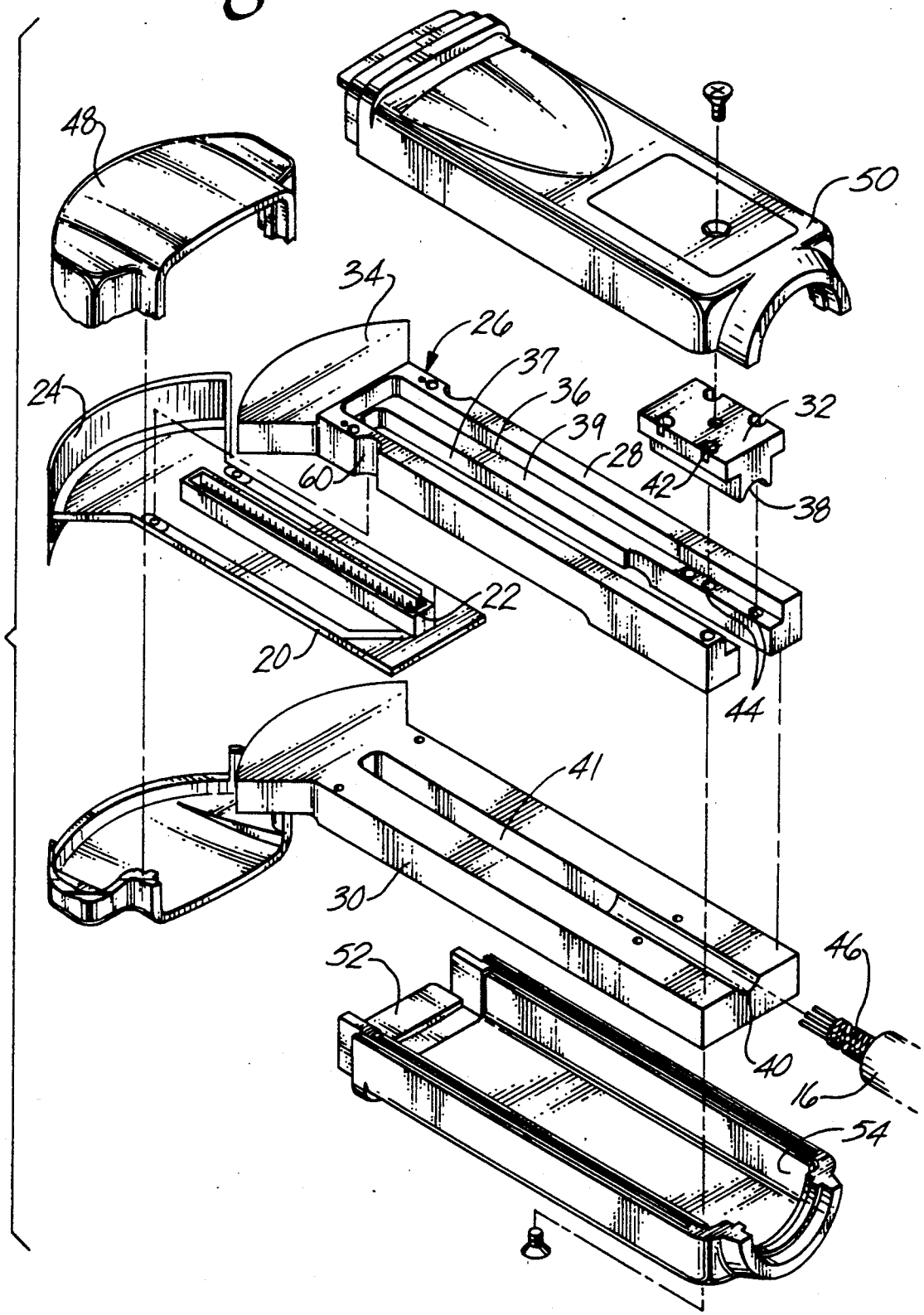
FIG. 2 is an exploded view of the transducer of FIG. 1.
Figure 3:
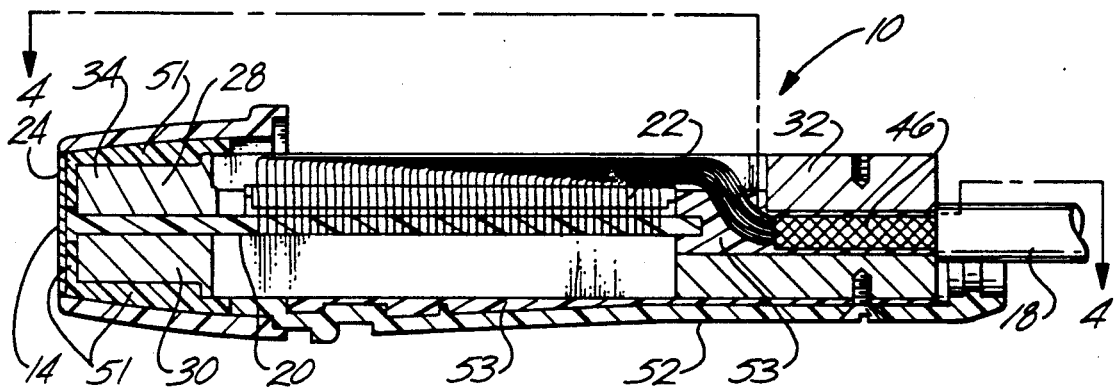
FIG. 3 is a longitudinal partial cross sectional view of taken through the middle transducer of FIG. 1.

As can be seen in FIGS. 2 and 3, the individual transducer elements 24 are electrically connected to a printed circuit board 20. The curved array elements could be manufactured from piezo-electric material by the method disclosed in U.S. Pat. No. 5,044,053, the disclosure of which is incorporated herein fully by reference. The printed circuit board extends rearwardly through a portion of the handle of the transducer. Mounted on the upper surface of the printed circuit board is a standard pin and socket connector 22. The pin and socket assembly serves as an electrical connection to the power cable. The electrical connections for the transducer elements and the power cable could alternatively be accomplished through the use of a flex circuit as disclosed in U.S. Pat. No. 5,044,053.

In operation, power is supplied to the transducer elements via the power cable, and during the scanning mode the ultrasonic transducer face temperature increases. The Federal Food and Drug Administration (FDA) has established regulatory standards for the face temperature of a transducer. This standard is that the face temperature of a transducer cannot exceed 41° C. The rate at which the face temperature of a transducer heats up is controlled by the power supplied to the transducer elements. Factors which also contribute to face temperature, which are characteristic to a particular transducer configuration in use, are frequency of the transducer, the physical size of the transducer and the type of material used to make the transducer. Applicants have found that transducers can exceed the FDA standard for face temperature in approximately seven minutes of operation at specific power settings. Therefore, for certain particular transducers to be maintained below FDA standards the transducers must be operated at less than an optimal power level. The problems that have arisen from operating the transducer at a less than optimal power level are that the depth of penetration of the ultrasonic signal and image quality are less than desirable. Normally, the optimum intensity limit of a transducer cannot be reached because face heating is the first limiting parameter exceeded. Consequently, a method for cooling the transducer is necessary so that the transducer can be operated at the optimum power level, while maintaining the face temperature of the transducer below the regulatory standards.

The method for cooling the ultrasonic transducer is accomplished by the following steps: First, a heat sink 26 is placed behind the transducer elements. In the preferred embodiment the heat sink is comprised of three separate pieces, namely an upper portion 28, a lower portion 30 and a braid clamp portion 32. The upper and lower portions of the heat sink are located a short distance (as close as possible) behind the transducer elements in the face of the transducer and extend rearwardly through the entire length of the handle. The upper and lower portions cover the upper and lower surfaces of the printed circuit board. The front surface 34 of the upper and lower portions of the heat sink is fan shaped, mirroring the curvature of the transducer elements. The upper portion of the heat sink has a stepped hollow interior 36 to allow room for the pin and socket connection of the printed circuit board and the wiring from the power cable. The stepped hollow interior has a slot 37 for the connector and a recess 39 for the wiring, shown in more detail in FIG. 4. The lower portion of the heat sink also has a slot 41 to allow in certain configurations the power cable to be wired to the bottom of the printed circuit board.

The braid clamp portion of the heat sink is T-shaped and is located in the rear portion of the stepped hollow interior of the upper portion of the heat sink. The braid clamp portion has a semi-circular groove 38 located along its lower surface which joins with an identical semicircular groove 40 located on the upper surface of the heat sink lower portion to form a channel through which the power cable may pass to the printed circuit board. The braided power cable is positioned in this channel while the wiring extending from the braid continues onto the connector 22. The braid clamp portion has a number of through holes 42 which are aligned with threaded holes 44 located in the stepped hollow interior of the heat sink upper portion which allow the braid clamp to clamp the power cord securely to the heat sink. The power cable is surrounded by braid 46 functioning as a radio frequency interference shield for the transducer, as well as a ground connection for the ultrasonic driving circuit. Clamping the heat sink to the braid provides strain relief for the braided cable.

Ideally, the heat sink material should possess as high a thermal capacity and as low a thermal resistance as possible. The heat sink material can be made from a copper/copper alloy, any aluminum alloy, or a silver/silver alloy. When considering other factors such as total weight of the assembly and cost of the heat sink unit, applicant has found that aluminum is the preferred metal for the heat sink.

The fan portion of the heat sink and the transducer elements are protected within a plastic housing 48. To achieve the desired damping characteristics and fill the cavity between the transducer elements and the heat sink a thermally loaded backing material 51 is injected into the cavity at the time of manufacture. The backing material is an epoxy loaded with heat conductive metal particles. The remaining portions of the heat sink are similarly protected by two pieces of plastic housing 50 and 52 which form the handle. The plastic of the housing is a specially formulated plastic in which the plastic itself also acts as a heat sink and is manufactured under the trade name MOBAY UT 1018. However, this plastic material does not have as good heat sink properties, i.e. as high heat capacity and as low a thermal resistance, as heat sink 26. Thus, the housing is at a lower temperature than heat sink 26 so it is comfortable for the operator to hold. The plastic material is also selected for its sanitary properties in a medical environment.

Before the plastic housing has been assembled around the heat sink a minimal cavity exists between the heat sink and the cable braid as well as between the plastic housing and the heat sink. To eliminate these cavities a heat conductive epoxy 53 is applied to the heat sink to fill these cavities. The epoxy is made heat conductive by containing metal particles. The conductive epoxy is commonly marketed under the trade name OMEGA-THERM 201. Alternatively, an aluminum lining 54 can be bonded to the inside surface of the plastic housing to provide a smooth surface in which to apply the thermal epoxy.

Figure 4:
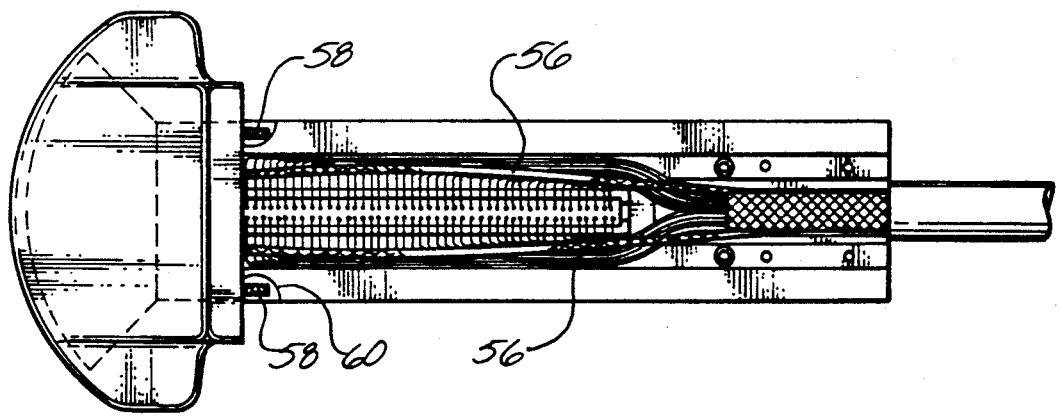
FIG. 4 is a top view of the transducer of FIG. 1 with the plastic housing removed.

The heat sink not only acts as a means for conductive heat transfer but also can be utilized as a ground connection for the transducer elements. Referring to FIG. 4, in previous embodiments ground wires 56 were connected to the cable braid and ground wires 58 are connected to the printed circuit board to make the ground connection. Presently, ground wires 56 are still connected to the cable braid but ground wires 58, extending from the transducer elements, are now connected to the heat sink along detent 60 on either side of the upper portion of the heat sink to make the ground connection. The ground wires can be connected by welding, bonding, mechanical attachment, or soldering techniques. Attaching the ground wires to the heat sink accomplishes a grounding effect along the entire length of the transducer. This grounding effect also increases the radio frequency interference shielding otherwise only accomplished by the power cable braid. In effect, the heat sink becomes an extension of the cable braid as far as radio frequency shielding is concerned.

In operation the heat generated in the face of the transducer is conducted away from the face via the heat sink and into the handle and the power cable. The heat from the transducer elements passes into the conductive epoxy behind the elements and then into the fan front of the heat sink. The heat is then transferred through the entire length of the heat sink before transferring through the epoxy and into the plastic housing. The heat is also conducted away from the heat sink by passing into the power cable braid and out the cable. Finally, the heat is dissipated into the surrounding air.

By conducting the heat away from the transducer face in the described manner, a greater amount of power can be supplied to the transducer elements while at the same time keeping the face temperature below federal standards. The benefits derived from incorporating this method include improved sensitivity, improved ultrasonic signal penetration, and improved image quality. Using this method results in operating the transducers at the optimum power level. This is especially important with large aperture transducers which require a larger amount of power to achieve effective intensity levels. As can be seen in FIG. 5 for a transducer having a 3.5 MHz frequency and using an aluminum heat sink, the face temperature does not reach 40° C. (which is below regulatory standards) until approximately 80 minutes of continuous use. It is also evident from the graph that the face temperature does not exceed the maximum 41° C. constraint. Similarly, the temperature of the heat sink, the plastic housing, and the power cable is maintained well below the temperature allowed for the face of the transducer.

The preceding description has been presented with reference to a presently preferred embodiment to the invention shown in the drawings. Workers skilled in the art and technology to which this invention pertains will appreciate that alterations and changes in the described structure can be practiced without departing from the spirit, principles and scope of this invention.

Accordingly, the foregoing description should not be read as pertaining only the precise structure described, but rather should be read consistent with and as support for, the following claims.

What is claimed is:

1. An ultrasonic medical transducer having improved heat transferability to cool the transducer comprising:
   a transducer face having a transducer element located therein and electrically connected to a braided power cable;
   a heat sink located behind the transducer element;
   a housing surrounding the heat sink; and
   heat conductive epoxy located between the housing and the heat sink.

2. An ultrasonic medical transducer of claim 1 wherein the heat sink is aluminum/aluminum alloy.

3. An ultrasonic medical transducer recited in claim 1 wherein the heat sink is copper/copper alloy.

4. An ultrasonic medical transducer as recited in claim 1 wherein the heat sink is comprised of three pieces.

5. An ultrasonic medical transducer as recited in claim 1 wherein the heat sink is secured to the power cable braid.

6. An ultrasonic medical transducer as recited in claim 1 wherein the transducer element is grounded to the heat sink to provide improved radio frequency interference shielding.

7. An ultrasonic medical transducer as recited in claim 1 wherein the transducer element is a curved array.

8. An ultrasonic medical transducer as recited in claim 1 wherein the transducer element is a linear array.

9. A method for manufacturing an ultrasonic medical transducer having improved heat transferability for cooling the transducer comprising the steps of:
   positioning a heat sink behind a transducer element;
   electrically connecting the transducer element to a braided power cable;
   applying a heat conductive epoxy to the heat sink; and
   assembling a housing around the heat sink.

10. A method for manufacturing an ultrasonic medical transducer as recited in claim 9 further comprising the steps of:
    applying a heat conductive epoxy to the braided power cable; and
    securing the heat sink to the braided power cable.

11. A method for manufacturing an ultrasonic medical transducer as recited in claim 9 wherein the heat sink is aluminum/aluminum alloy.

12. A method for manufacturing an ultrasonic medical transducer as recited in claim 9 wherein the heat sink is copper/copper alloy.

13. A method for manufacturing an ultrasonic medical transducer as recited in claim 9 wherein the heat sink comprises three pieces.

14. A method for manufacturing an ultrasonic medical transducer as recited in claim 9 further comprising the step of grounding the transducer element to the heat sink.

15. A method for manufacturing an ultrasonic medical transducer as recited in claim 10 wherein the step of securing the heat sink to the power cable comprises the step of clamping the heat sink to the braided power cable.

16. A method of transferring heat away from an ultrasonic medical transducer having a face wherein heat is generated, a heat sink located behind the transducer face, a braided power cable secured to the heat sink, a housing surrounding the heat sink, and heat conductive epoxy located between the heat sink and the housing comprising the steps of:
    transferring the heat from the transducer face to the heat sink;
    transferring the heat from the heat sink to the heat conductive epoxy;
    transferring the heat from the heat conductive epoxy to the braided power cable;
    transferring the heat from the heat conductive epoxy to the housing; and
    dissipating the heat from the braided power cable and the housing into the surrounding air.

17. An ultrasonic medical transducer having improved heat transfer characteristics, the transducer comprising:
    an array of ultrasound transducer elements;
    a handle shaped heat sink in heat conductive relationship with the array; and
    a handle surrounding the heat sink in heat conductive relationship therewith, the handle being made of a material having a lower thermal capacity than the heat sink.

18. The ultrasonic transducer of claim 17, in which the material of the handle has a higher heat resistivity than the heat sink.

19. The ultrasonic transducer of claim 17, additionally comprising a cable electrically connected to the array, the cable having an electrically grounded conductor in heat conductive relationship to the heat sink to transfer heat from the array to the cable.

20. The ultrasonic transducer of claim 19, in which the grounded conductor is a braided sheath around the cable.

21. The ultrasonic transducer of claim 17, additionally comprising a power cable, an electrical connector for electrically connecting the array to the power cable, and a cavity in the heat sink in which the connector is disposed.

22. The ultrasonic transducer of claim 21, in which the cavity is located so the heat sink surrounds the connector mechanism.

23. An ultrasonic medical transducer having improved heat transfer characteristics, the transducer comprising:
    an array of ultrasound transducer elements;

a handle shaped heat sink in heat conductive relationship with the array; and a handle surrounding the heat sink in heat conductive relationship therewith, the handle being made of a material having a higher thermal resistance than the heat sink.

24. An ultrasonic medical transducer having improved heat transfer characteristics, the transducer comprising:

an array of ultrasound transducer elements;

a heat sink in heat conductive relationship with the array; and a cable electrically connected to the array, the cable having an electrically grounded conductor in heat conductive relationship to the heat sink to transfer heat from the array to the cable.

25. The ultrasonic transducer of claim 24, in which the grounded conductor is a braided sheath around the cable.

* * * * *